United States Patent
Johnson et al.

(10) Patent No.: US 8,624,052 B2
(45) Date of Patent: Jan. 7, 2014

(54) S-T-BUTYL PROTECTED CYSTEINE DI-PEPTIDE ANALOGS AND RELATED COMPOUNDS

(75) Inventors: Edward M. Johnson, Glendale, WI (US); Daniel G. Lawton, Bayside, WI (US)

(73) Assignee: Promentis Pharmaceuticals, Inc., Milwaukee, WI (US)

(*) Notice: Subject to any disclaimer, the term of this patent is extended or adjusted under 35 U.S.C. 154(b) by 41 days.

(21) Appl. No.: 13/294,868

(22) Filed: Nov. 11, 2011

(65) Prior Publication Data

US 2012/0122792 A1  May 17, 2012

Related U.S. Application Data

(60) Provisional application No. 61/413,152, filed on Nov. 12, 2010.

(51) Int. Cl.
*C07C 205/02* (2006.01)
*C07C 321/00* (2006.01)

(52) U.S. Cl.
USPC .......................................... 560/147; 560/156

(58) Field of Classification Search
USPC .................................. 548/100; 560/147, 156
See application file for complete search history.

(56) References Cited

U.S. PATENT DOCUMENTS

2009/0281109 A1* 11/2009 Cook et al. ............... 514/252.11

* cited by examiner

*Primary Examiner* — Yong Chu
*Assistant Examiner* — Sonya Wright
(74) *Attorney, Agent, or Firm* — Wood, Phillips, Katz, Clark & Mortimer

(57) ABSTRACT

S-t-butyl protected cysteine di-peptide analogs and related compounds and methods of using these compounds for the treatment of diseases and/or conditions, including but not limited to diseases and/or conditions of Central Nervous System (CNS).

2 Claims, No Drawings

S-T-BUTYL PROTECTED CYSTEINE DI-PEPTIDE ANALOGS AND RELATED COMPOUNDS

FIELD OF THE INVENTION

This invention relates to novel S-t-butyl protected cysteine di-peptide analogs and related compounds and methods of using these compounds for the treatment of diseases and/or conditions, including but not limited to diseases and/or conditions of Central Nervous System (CNS).

BACKGROUND OF THE INVENTION

Diseases and/or conditions of the Central Nervous System (CNS) affect a large number of people. One of the CNS disorders, schizophrenia, is a debilitating disorder afflicting 1% of the world's population. The development of effective medications to treat schizophrenia relies on advances in characterizing the underlying pathophysiology.

Conventional approaches to treating schizophrenia and other CNS disorders have significant disadvantages, including suboptimal efficacy and/or side effects associated with their use. For example, existing first and second generation antipsychotic agents have a number of shortcomings and significant side effects, such as extrapyramidal side effects, endocrine effects, obesity, elevated triglycerides, blood pressure and glucose levels, type II diabetes, cardiovascular disease, renal toxicity and agranulocytosis. Thus, it is desirable to develop novel agents that can improve treatment outcomes and safety.

Accordingly, there is a significant need for new therapeutical agents to treat disorders of the CNS.

SUMMARY OF THE INVENTION

In one aspect, the present invention is directed to compounds of formula I:

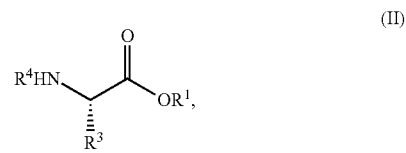

(I)

where
$R^1$ is selected from the group consisting of $CH_3$, $CH_2CH_3$, $CH(CH_3)_2$, $CH_2$-phenyl, and phenyl;
$R^4$ is selected from the group consisting of H, $C(O)R_2$, and

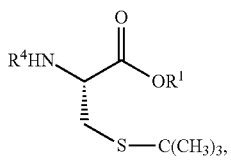

$R^2$ is selected from the group consisting of $CH_3$, $CH_2CH_3$, $CH(CH_3)_2$, $CH_2$-phenyl, and phenyl; and
$R^3$ is selected from the group consisting of H, $CH_3$, $CH_2$-phenyl, $CH(CH_3)_2$, $CH_2OH$,

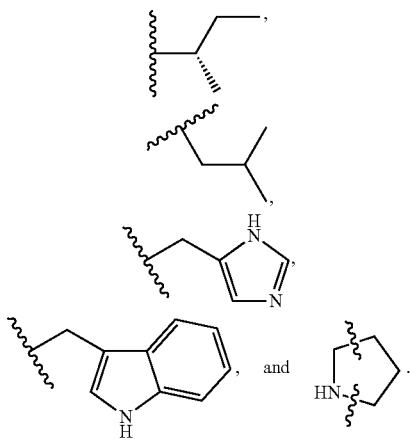

In another aspect, the present invention is directed to compounds of formula II:

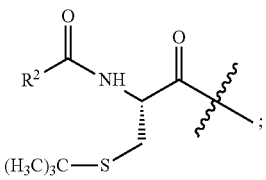

(II)

where
$R^1$ is selected from the group consisting of $CH_3$, $CH_2CH_3$, $CH(CH_3)_2$, $CH_2$-phenyl, and phenyl;
$R^4$ is selected from the group consisting of H and

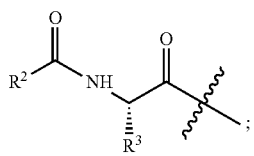

$R^2$ is selected from the group consisting of $CH_3$, $CH_2CH_3$, $CH(CH_3)_2$, $CH_2$-phenyl, and phenyl; and
$R^3$ is selected from the group consisting of H, $CH_3$, $CH_2$-phenyl, $CH(CH_3)_2$, $CH_2OH$,

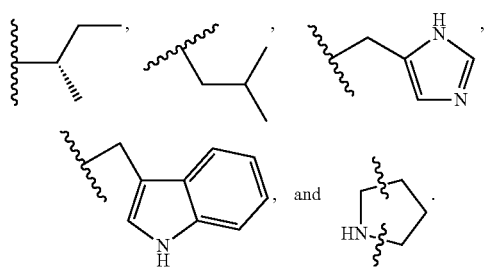

The invention also encompasses pharmaceutically acceptable salts, esters and prodrugs of the provided compounds.

In another aspect, the invention is directed to a method of treating a disease or condition in a subject comprising administering to the subject a therapeutically effective amount of a compound of any of Formulas I or II or a pharmaceutically acceptable salt thereof. The preferred route of administering to the subject is via oral delivery. Preferably, diseases or conditions treatable with the compounds of the present invention are related to central nervous system (CNS).

In another aspect, the present invention provides methods of treating a disease or condition of the Central Nervous System (CNS), including but not limited to schizophrenia, drug craving, drug addiction, bipolar disorder, anxiety, depression, Parkinson's disease, Alzheimer's disease, cognitive dysfunction, multiple sclerosis, Amyotrophic lateral sclerosis (ALS), ischemic stroke, HIV dementia, and Huntington's disease comprising administering to a subject in need thereof a therapeutically effective amount of any of the inventive compounds.

In a preferred embodiment, the disease is schizophrenia.

In some aspects, the methods and compositions of the invention may be used in combination with conventional first and second generation anti-psychotic agents.

Thus, in one embodiment, the invention is directed to a combinational use of: 1) a compound of any of Formulas I-II and 2) pre-existing first generation anti-psychotic agents (including but not limited to chlorpromazine, thioridazine, mesoridazine, loxapine, molindone, perphenazine, thiothixene, trifluoperazine, haloperidol, fluphenazine, droperidol, zuclopenthixol and prochlorperazineperphenazine) and/or second generation anti-psychotic agents (including but not limited to amisulpride, aripiprazole, asenapine, blonanserin, clotiapine, clozapine, iloperidone, lurasidone, mosapramine, olanzapine, paliperidone, perospirone, quetiapine, remoxipride, risperidone, sertindole, sulpiride, ziprasidone, zotepine, bifeprunox (DU-127,090), pimavanserin (ACP-103), and vabicaserin (SCA-136) for the treatment of a disease or condition of CNS, including but not limited to schizophrenia, drug craving, drug addiction, bipolar disorder, anxiety, depression, Parkinson's disease, Alzheimer's disease, cognitive dysfunction, multiple sclerosis, ALS, ischemic stroke, HIV dementia, and Huntington's disease.

The invention further encompasses pharmaceutical compositions containing a compound of any of Formulas I or II or a pharmaceutically acceptable salt thereof in combination with a pharmaceutically-acceptable carrier.

Methods of formulating/manufacturing such pharmaceutical compositions (alternatively termed "medicaments") for the treatment of a disease or condition in a subject are also within the invention's scope.

DETAILED DESCRIPTION OF THE INVENTION

The following definitions are used, unless otherwise described.

The term "t-butyl" refers to tert-butyl alkyl group.

The term "DBU" refers to 1,8-diazabicyclo[5.4.0]undec-7-ene.

The term "CDI" refers to 1,1'-carbonyldiimidazole.

The term "HOBt" refers to hydroxybenzotriazole.

The term "EDCI" refers to 1-ethyl-3-(3-dimethylaminopropyl)carbodiimide, which is a coupling agent.

The term "prodrugs" refers to compounds, including but not limited to monomers and dimers of the compounds of the invention, which become under physiological conditions compounds of the invention or the active moieties of the compounds of the invention.

The term "active moieties" refers to compounds which are pharmaceutically active in vivo, whether or not such compounds are compounds of the invention.

The term "ester" refers to compounds having a generic structure of $RCO_2R'$, where R and R' are the organic parts of the carboxylic acid and alcohol respectively.

The term "dimer" refers to the chemical entity formed by disulfide linkage of two identical prodrugs, or protected cysteine analogs described herein.

The term "subject" includes humans. The terms "human," "patient" and "subject" are used interchangeably.

In general, unless indicated otherwise, a chemical group referred to anywhere in the specification can be optionally substituted.

The term "therapeutically effective amount" means the amount of a compound that, when administered to a subject for treating a disease or disorder, is sufficient to effect such treatment for the disease or disorder. The "therapeutically effective amount" can vary depending on the compound, the disease or disorder and its severity, and the age, weight, etc., of the subject to be treated.

In one embodiment, the terms "treating" or "treatment" refer to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

In one aspect, the present invention is directed to compounds of formula I:

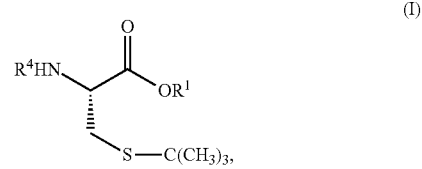

(I)

where $R^1$ is selected from the group consisting of $CH_3$, $CH_2CH_3$, $CH(CH_3)_2$, $CH_2$-phenyl, and phenyl, $R^4$ is selected from the group consisting of H, $C(O)R_2$, and

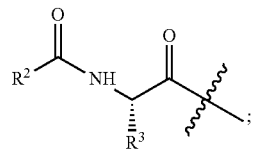

;

$R^2$ is selected from the group consisting of $CH_3$, $CH_2CH_3$, $CH(CH_3)_2$, $CH_2$-phenyl, and phenyl; and $R^3$ is selected from the group consisting of H, $CH_3$, $CH_2$-phenyl, $CH(CH_3)_2$, $CH_2OH$,

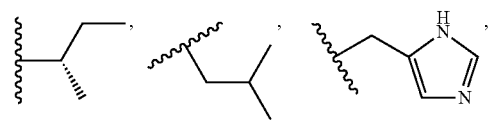

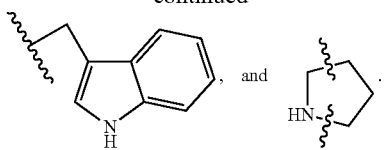

In another aspect, the present invention is directed to compounds of formula II:

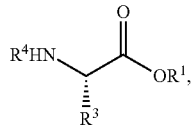
(II)

where
$R^1$ is selected from the group consisting of $CH_3$, $CH_2CH_3$, $CH(CH_3)_2$, $CH_2$-phenyl, and phenyl;
$R^4$ is selected from the group consisting of H and

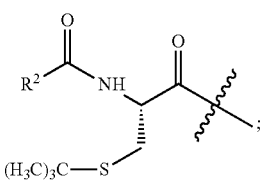

$R^2$ is selected from the group consisting of $CH_3$, $CH_2CH_3$, $CH(CH_3)_2$, $CH_2$-phenyl, and phenyl; and
$R^3$ is selected from the group consisting of H, $CH_3$, $CH_2$-phenyl, $CH(CH_3)_2$, $CH_2OH$,

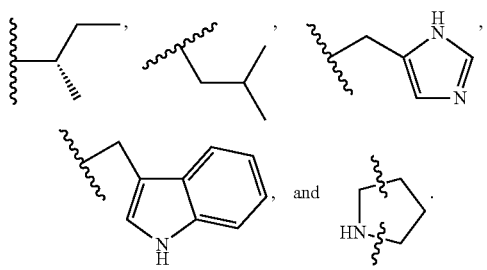

Presently preferred compounds include:

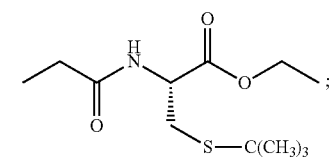

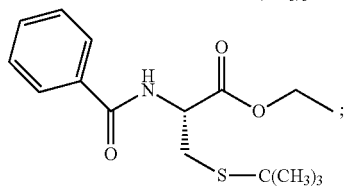

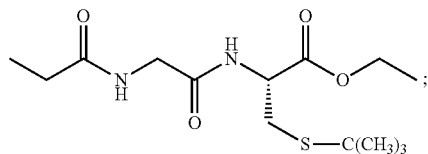

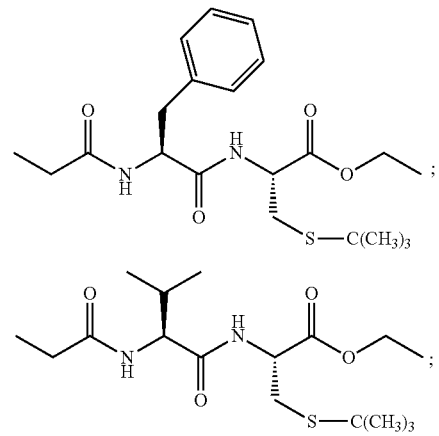

-continued

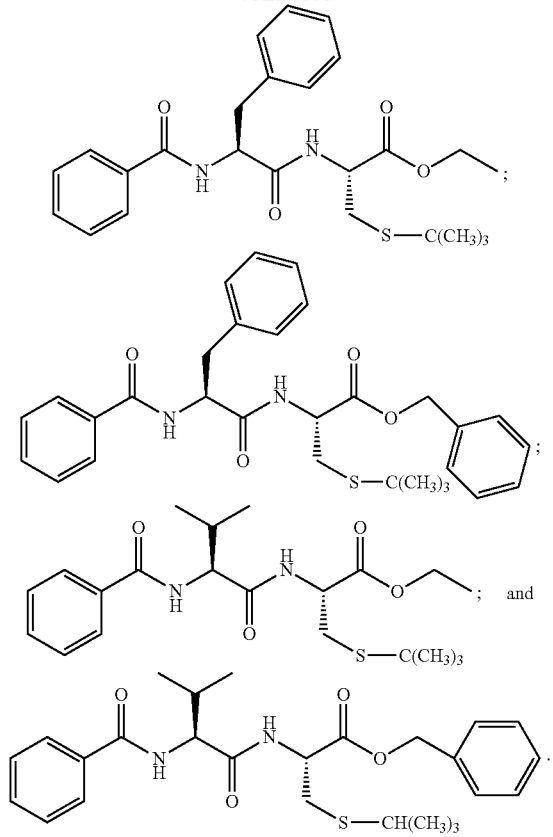

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by formulas above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers are included within the scope of the compounds of the formulas above.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.)

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, transdermally (e.g. using a patch), transmucosally, sublingually, pulmonary, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

In another aspect, the invention is directed to a method of treating a disease or condition in a subject comprising administering to the subject a therapeutically effective amount of a compound of any of Formulas I or II or a pharmaceutically acceptable salt thereof. The preferred route of administering to the subject is via oral delivery.

In particular, the present invention provides methods of treating a disease or condition of the Central Nervous System (CNS), including but not limited to schizophrenia, drug craving, drug addiction, bipolar disorder, anxiety, depression, Parkinson's disease, Alzheimer's disease, cognitive dysfunction, multiple sclerosis, Amyotrophic lateral sclerosis (ALS), ischemic stroke, HIV dementia, and Huntington's disease comprising administering to a subject in need thereof a therapeutically effective amount of any of the inventive compounds.

However, it is within a skill in the art that the provided compounds may be used to treat other diseases or conditions associated with diminished glutathione levels and/or glutamate signaling, and/or oxidative stress, and/or impaired cystine-glutamate antiporter activity, glutamate neurotransmission, synaptic connection, and gene expression.

In general, the invention is not limited to treatment of any specific disease or condition but encompasses the treatment of any disease or condition whose mechanism may be affected by the compounds of the present invention.

In some aspects, the methods and compositions of the invention may be used in combination with conventional first and second generation anti-psychotic agents.

Thus, in one embodiment, the invention is directed to a combinational use of: 1) a compound of any of Formulas I-II and 2) pre-existing first generation anti-psychotic agents (including but not limited to chlorpromazine, thioridazine, mesoridazine, loxapine, molindone, perphenazine, thiothixene, trifluoperazine, haloperidol, fluphenazine, droperidol, zuclopenthixol and prochlorperazineperphenazine) and/or second generation anti-psychotic agents (including but not limited to amisulpride, aripiprazole, asenapine, blonanserin, clotiapine, clozapine, iloperidone, lurasidone, mosapramine, olanzapine, paliperidone, perospirone, quetiapine, remoxipride, risperidone, sertindole, sulpiride, ziprasidone, zotepine, bifeprunox (DU-127,090), pimavanserin (ACP-103), and vabicaserin (SCA-136)) for the treatment of a disease or condition of CNS, including but not limited to schizophrenia, drug craving, drug addiction, bipolar disorder, anxiety, depression, Parkinson's disease, Alzheimer's disease, cognitive dysfunction, multiple sclerosis, ALS, ischemic stroke, HIV dementia, and Huntington's disease.

The invention further encompasses pharmaceutical compositions containing a compound of any of Formulas I or II or a pharmaceutically acceptable salt thereof in combination with a pharmaceutically-acceptable carrier.

Methods of formulating/manufacturing such pharmaceutical compositions (alternatively termed "medicaments") for the treatment of a disease or condition in a subject are also within the invention's scope.

For a clearer understanding of the invention, details are provided below. These are merely illustrations and are not to be understood as limiting the scope of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Exemplary synthetic strategies are outlined in Schemes 1-3 which yield S-t-butyl protected cysteine di-peptide analogs according to the present invention. No representation has been made that the actual synthesis following Schemes 1-3 has been performed. However, it is believed that a person of skill in the art would know how to synthesize the claimed compounds based, in part, on the provided Schemes 1-3.

Schemes 4-10 illustrate the actual synthesis that has been performed to make some of the compounds of the invention.

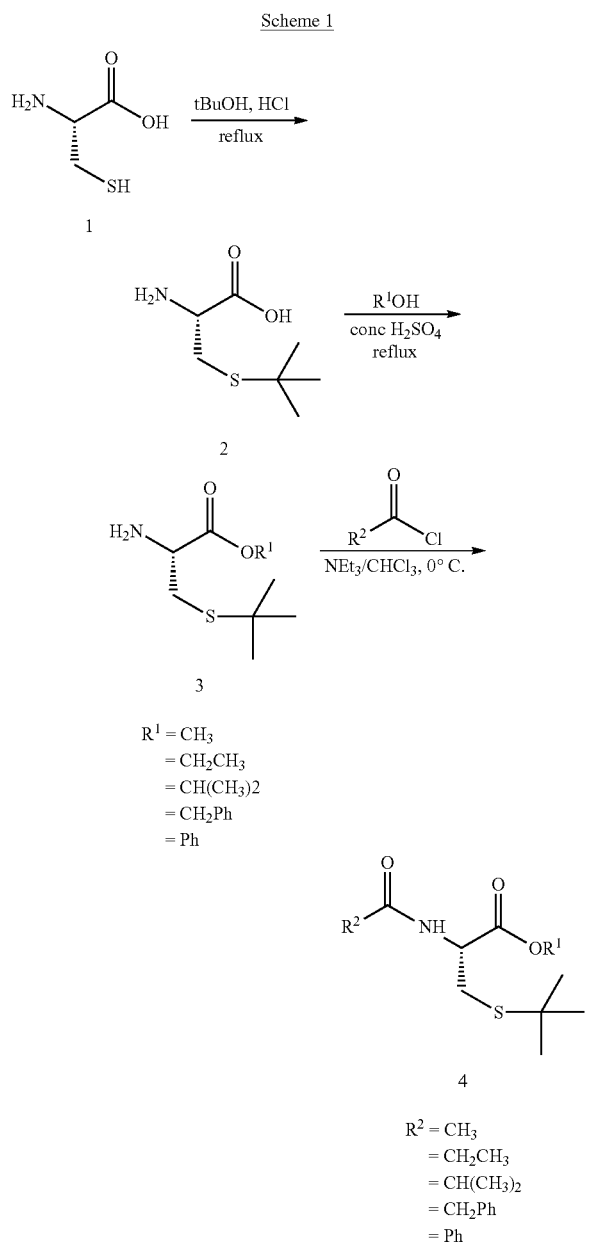

where
tBuOH is tert-butanol and
$R^1$ and $R^2$ are independently selected from the group consisting of $CH_3$, $CH_2CH_3$, $CH(CH_3)_2$, $CH_2$-phenyl, and phenyl.
Description of Reactions in Scheme 1

Cysteine (I) is dissolved in a large excess of concentrated (12 N) hydrochloric acid and is treated with a solution of tert-butanol (dissolved in 12 N hydrochloric acid) at room temperature while stirring. After the addition of tert-butanol, the mixture is heated to reflux for 6 hrs while stirring. When the reaction is completed, the mixture is cooled to 0° C. and the precipitating solid, the S-t-butyl cysteine (2), is filtered off from the remaining solution.

The S-t-butyl protected cysteine (2) is dissolved in anhydrous concentrated sulfuric acid and treated with 1.5 molar equivalent of the corresponding alcohol ($R^1OH$) drop wise while stirring. After the alcohol addition, the mixture is allowed to stir under an argon atmosphere for 8-12 hrs to ensure reaction completion. The mixture is then added to an ice water bath to stop and cool the reaction. The resulting mixture is extracted with methylene chloride (×3) to remove the desired compound (3) from the water layer. The organic level is dried over magnesium sulfate (or potassium carbonate) and filtered. The resulting organic solution is condensed under vacuum and solvent is removed from the desired compound (3). The desired compound (3) is carried over to the next reaction without additional purification.

The freshly obtained compound (3) is added to a mixture of triethylamine and chloroform (1:2) and cooled with an ice bath to 0° C. The resulting mixture is treated with 1.1 molar equivalent of the corresponding acyl chloride ($R^2C(O)Cl$) while stirring under an argon atmosphere for 4-6 hrs to produce the desired compound (4). After the reaction is completed, ice water is added to the mixture and the desired compound (4) is extracted with methylene chloride (×3) and dried over magnesium sulfate (potassium carbonate). The final product is obtained by removing the solvent under vacuum to obtain compound (4).

Synthesis of Compound 4 where $R^1$ and $R^2$ are Methyl

Compound 4 where $R^1$ and $R^2$ are methyl may be prepared, for example, as follows:

Cysteine (1) is dissolved in a large excess of concentrated (12 N) hydrochloric acid and is treated with a solution of tert-butanol (dissolved in 12 N hydrochloric acid) at room temperature while stirring. After the addition of tert-butanol, the mixture is heated to reflux for 6 hrs while stirring. When the reaction is completed, the mixture is cooled to 0° C. and the precipitating solid, the S-t-butyl cysteine (2), is filtered off from the remaining solution.

The S-t-butyl protected cysteine (2) is dissolved in anhydrous concentrated sulfuric acid and treated with 1.5 molar equivalent of methyl alcohol ($CH_3OH$) drop wise while stirring. After the alcohol addition, the mixture is allowed to stir under an argon atmosphere for 8-12 hrs to ensure reaction completion. The mixture is then added to an ice water bath to stop and cool the reaction. The resulting mixture is extracted with methylene chloride (×3) to remove the desired compound (3) from the water layer. The organic level is dried over magnesium sulfate (or potassium carbonate) and filtered. The resulting organic solution is condensed under vacuum and solvent is removed from the desired compound (3). The desired compound (3) is carried over to the next reaction without additional purification.

The freshly obtained compound (3) is added to a mixture of triethylamine and chloroform (1:2) and cooled with an ice bath to 0° C. The resulting mixture is treated with 1.1 molar equivalent acetyl chloride while stirring under an argon atmosphere for 4-6 hrs to produce the desired compound (4). After the reaction is completed, ice water is added to the mixture and the desired compound (4) is extracted with methylene chloride (×3) and dried over magnesium sulfate (potassium carbonate). The final product is obtained by removing the solvent under vacuum to obtain compound (4).

Scheme 2

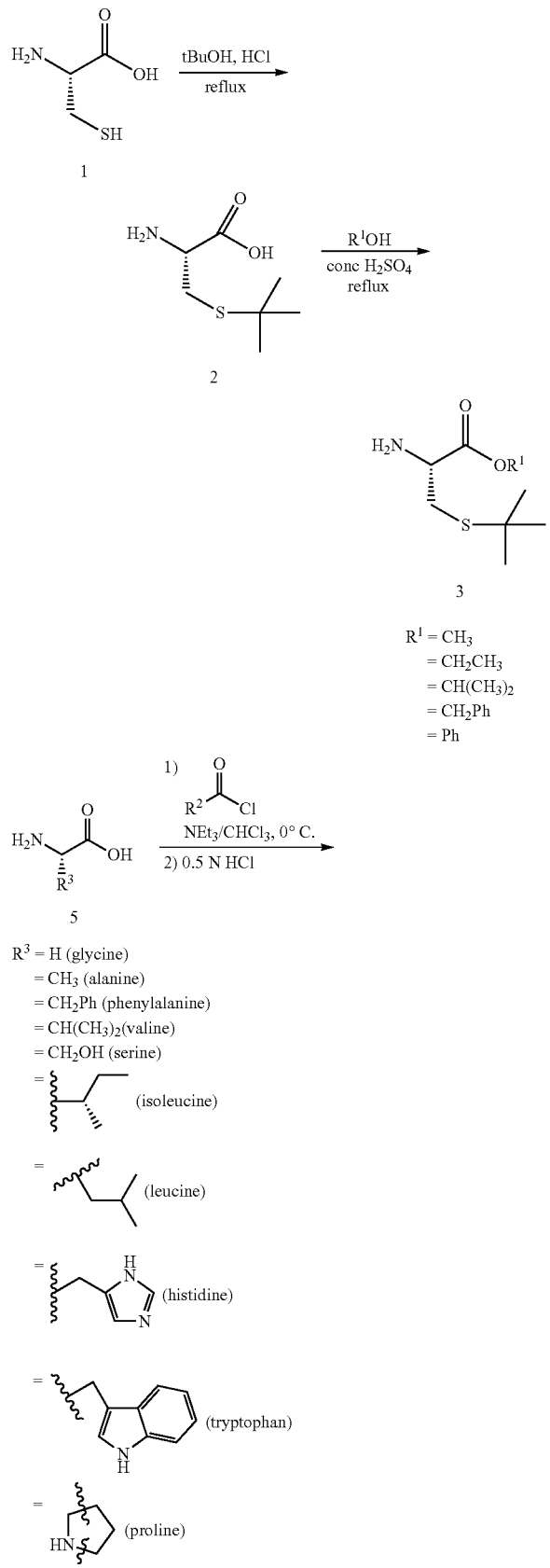

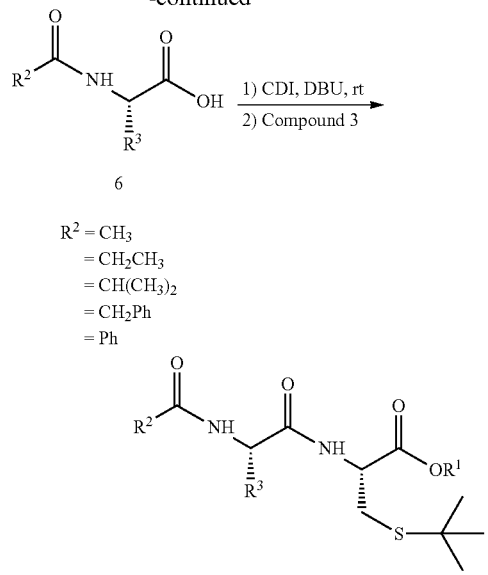

$R^2 = CH_3$
$\quad = CH_2CH_3$
$\quad = CH(CH_3)_2$
$\quad = CH_2Ph$
$\quad = Ph$

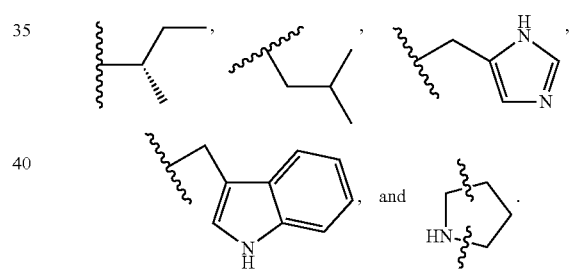

where
$R^1$ and $R^2$ are independently selected from the group consisting of $CH_3$, $CH_2CH_3$, $CH(CH_3)_2$, $CH_2$-phenyl, and phenyl; and
$R^3$ is selected from the group consisting of H, $CH_3$, $CH_2$-phenyl, $CH(CH_3)_2$, $CH_2OH$,

Description of Reactions in Scheme 2

Cysteine (1) is dissolved in a large excess of concentrated (12 N) hydrochloric acid and is treated with a solution of tert-butanol (dissolved in 12 N hydrochloric acid) at room temperature while stirring. After the addition of tert-butanol, the mixture is heated to reflux for 6 hrs while stirring. When the reaction is completed, the mixture is cooled to 0° C. and the precipitating solid, the S-t-butyl cysteine (2), is filtered off from the remaining solution.

The S-t-butyl protected cysteine (2) is dissolved in anhydrous concentrated sulfuric acid and treated with 1.5 molar equivalent of the corresponding alcohol ($R^1OH$) drop wise while stirring. After the alcohol addition, the mixture is allowed to stir under an argon atmosphere for 8-12 hrs to ensure reaction completion. The mixture is then added to an ice water bath to stop and cool the reaction. The resulting mixture is extracted with methylene chloride (×3) to remove the desired compound (3) from the water layer. The organic level is dried over magnesium sulfate (or potassium carbonate) and filtered. The resulting organic solution is condensed under vacuum and solvent is removed from the desired compound (3). The desired compound (3) is carried over to the next reaction without additional purification.

The desired amino acid (5) is added to a mixture of triethylamine and chloroform (1:2) and cooled with an ice bath to 0° C. The resulting mixture is treated with 1.1 molar equivalent of the corresponding acyl chloride ($R^2C(O)Cl$) while stirring under an argon atmosphere for 4-6 hrs. After the reaction is completed, the mixture is treated with 0.5 N HCl to liberate the carboxylic acid group for future reactions, producing the desired compound (6). The resulting compound (6) is dissolved in stirring methylene chloride and treating with 1.2 molar equivalent of 1,1'-carbonyldiimidazole (CDI) and 1.1 equivalent of 1,8-diazabicyclo[5.4.0]undec-7-ene (DBU) at room temperature and allowed to stir for 4 hrs under an argon atmosphere. After the initial reaction is completed, freshly prepared compound (3) (1.2 molar equivalent) is added slowly to the reaction at room temperature while stirring. The resulting mixture is allowed to stir for an additional 4 hrs to produce the desired compound (7).

Synthesis of Compound 7 where $R^1$ and $R^2$ are Methyl, $R^3$ is H

To make compound 7 where W and $R^2$ are methyl and $R^3$ is hydrogen, the following steps may be taken:

Cysteine (1) is dissolved in a large excess of concentrated (12 N) hydrochloric acid and is treated with a solution of tert-butanol (dissolved in 12 N hydrochloric acid) at room temperature while stirring. After the addition of tert-butanol, the mixture is heated to reflux for 6 hrs while stirring. When the reaction is completed, the mixture is cooled to 0° C. and the precipitating solid, the S-t-butyl cysteine (2), is filtered off from the remaining solution.

The S-t-butyl protected cysteine (2) is dissolved in anhydrous concentrated sulfuric acid and treated with 1.5 molar equivalent of methyl alcohol ($CH_3OH$) drop wise while stirring. After the alcohol addition, the mixture is allowed to stir under an argon atmosphere for 8-12 hrs to ensure reaction completion. The mixture is then added to an ice water bath to stop and cool the reaction. The resulting mixture is extracted with methylene chloride (×3) to remove the desired compound (3) from the water layer. The organic level is dried over magnesium sulfate (or potassium carbonate) and filtered. The resulting organic solution is condensed under vacuum and solvent is removed from the desired compound (3). The desired compound (3) is carried over to the next reaction without additional purification.

The desired amino acid, glycine (5) is added to a mixture of triethylamine and chloroform (1:2) and cooled with an ice bath to 0° C. The resulting mixture is treated with 1.1 molar equivalent of acetyl chloride while stirring under an argon atmosphere for 4-6 hrs. After the reaction is completed, the mixture is treated with 0.5 N HCl to liberate the carboxylic acid group for future reactions, producing the desired compound (6). The resulting compound (6) is dissolved in stirring methylene chloride and treating with 1.2 molar equivalent of 1,1'-carbonyldiimidazole (CDI) and 1.1 equivalent of 1,8-diazabicyclo[5.4.0]undec-7-ene (DBU) at room temperature and allowed to stir for 4 hrs under an argon atmosphere. After the initial reaction is completed, freshly prepared compound (3) (1.2 molar equivalent) is added slowly to the reaction at room temperature while stirring. The resulting mixture is allowed to stir for an additional 4 hrs to produce the desired compound (7).

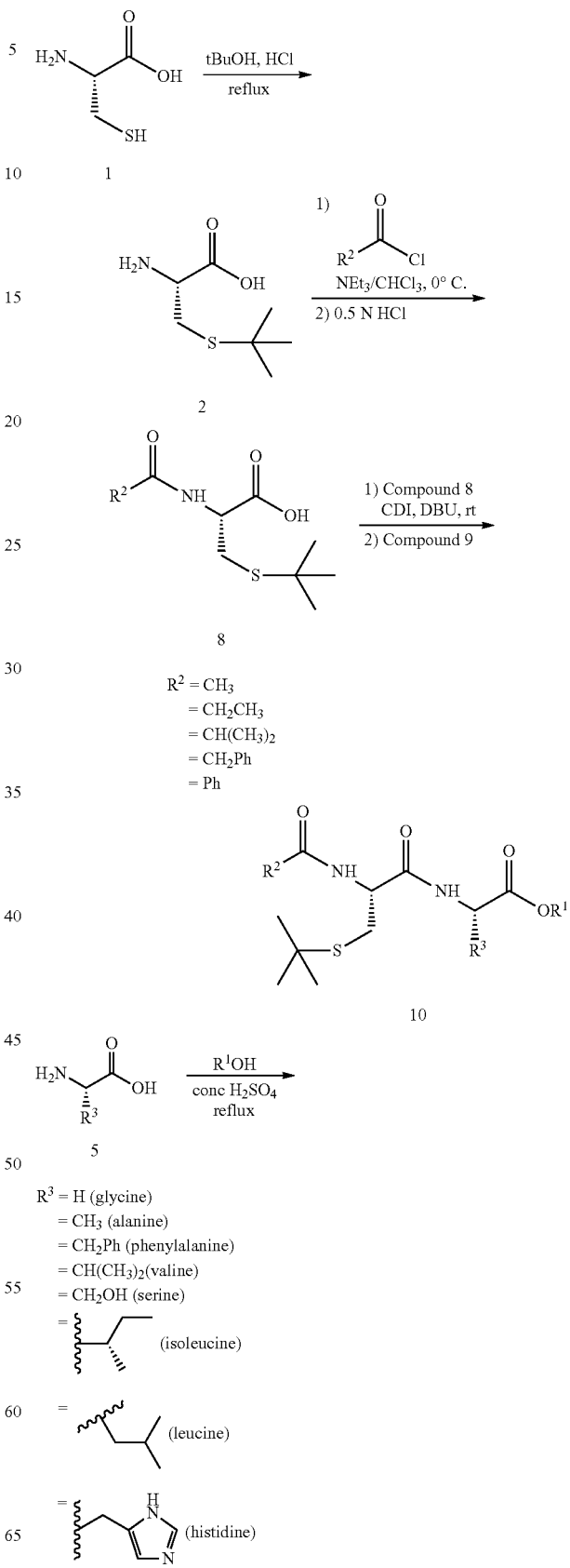

-continued

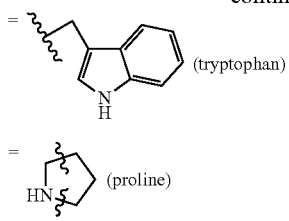
(tryptophan)

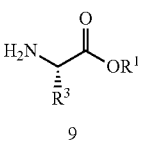
(proline)

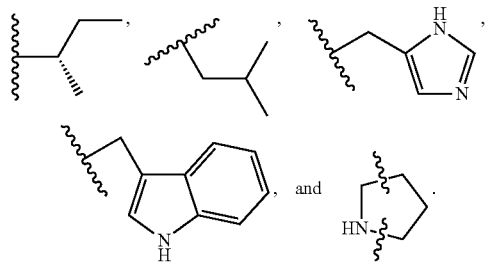

$R^1 = CH_3$
$= CH_2CH_3$
$= CH(CH_3)_2$
$= CH_2Ph$
$= Ph$ where
$R^1$ and $R^2$ are independently selected from the group consisting of $CH_3$, $CH_2CH_3$, $CH(CH_3)_2$, $CH_2$-phenyl, and phenyl; and
$R^3$ is selected from the group consisting of H, $CH_3$, $CH_2$-phenyl, $CH(CH_3)_2$, $CH_2OH$,

Description of Reactions in Scheme 3

Cysteine (1) is dissolved in a large excess of concentrated (12 N) hydrochloric acid and is treated with a solution of tert-butanol (dissolved in 12 N hydrochloric acid) at room temperature while stirring. After the addition of tert-butanol, the mixture is heated to reflux for 6 hrs while stirring. When the reaction is completed, the mixture is cooled to 0° C. and the precipitating solid, the S-t-butyl cysteine (2), is filtered off from the remaining solution.

The desired amino acid (5) is dissolved in anhydrous concentrated sulfuric acid and treated with 1.5 molar equivalent of the corresponding alcohol ($R^1OH$) drop wise while stirring. After the alcohol addition, the mixture is allowed to stir under an argon atmosphere for 8-12 hrs to ensure reaction completion. The mixture is then added to an ice water bath to stop and cool the reaction. The resulting mixture is extracted with methylene chloride (×3) to remove the desired compound (9) from the water layer. The organic level is dried over magnesium sulfate (or potassium carbonate) and filtered. The resulting organic solution is condensed under vacuum and solvent is removed from the desired compound (9). The desired compound (9) is carried over to the next reaction without additional purification.

The S-t-butyl protected cysteine (2) is added to a mixture of triethylamine and chloroform (1:2) and cooled with an ice bath to 0° C. The resulting mixture is treated with 1.1 molar equivalent of the corresponding acyl chloride ($R^2C(O)Cl$) while stirring under an argon atmosphere for 4-6 hrs. After the reaction is completed, the mixture is treated with 0.5 N HCl to liberate the carboxylic acid group for future reactions, producing the desired compound (8). The resulting compound (8) is dissolved in stirring methylene chloride and treating with 1.2 molar equivalent of 1,1'-carbonyldiiminidazole (CDI) and 1.1 equivalent of 1,8-diazabicyclo[5.4.0]undec-7-ene (DBU) at room temperature and allowed to stir for 4 hrs under an argon atmosphere. After the initial reaction is completed, freshly prepared compound (9) (1.2 molar equivalent) is added slowly to the reaction at room temperature while stirring. The resulting mixture is allowed to stir for an additional 4 hrs to produce the desired compound (10).

Synthesis of Compound 10 where $R^1$ and $R^2$ are Methyl and $R^3$ is H

To synthesize compound 10 where $R^1$ and $R^2$ are methyl and $R^3$ is H, the following steps may be taken:

Cysteine (1) is dissolved in a large excess of concentrated (12 N) hydrochloric acid and is treated with a solution of tert-butanol (dissolved in 12 N hydrochloric acid) at room temperature while stirring. After the addition of tert-butanol, the mixture is heated to reflux for 6 hrs while stirring. When the reaction is completed, the mixture is cooled to 0° C. and the precipitating solid, the S-t-butyl cysteine (2), is filtered off from the remaining solution.

The desired amino acid, glycine (5) is dissolved in anhydrous concentrated sulfuric acid and treated with 1.5 molar equivalent of methyl alcohol ($CH_3OH$) drop wise while stirring. After the alcohol addition, the mixture is allowed to stir under an argon atmosphere for 8-12 hrs to ensure reaction completion. The mixture is then added to an ice water bath to stop and cool the reaction. The resulting mixture is extracted with methylene chloride (×3) to remove the desired compound (9) from the water layer. The organic level is dried over magnesium sulfate (or potassium carbonate) and filtered. The resulting organic solution is condensed under vacuum and solvent is removed from the desired compound (9). The desired compound (9) is carried over to the next reaction without additional purification.

The S-t-butyl protected cysteine (2) is added to a mixture of triethylamine and chloroform (1:2) and cooled with an ice bath to 0° C. The resulting mixture is treated with 1.1 molar equivalent of acetyl chloride while stirring under an argon atmosphere for 4-6 hrs. After the reaction is completed, the mixture is treated with 0.5 N HCl to liberate the carboxylic acid group for future reactions, producing the desired compound (8). The resulting compound (8) is dissolved in stirring methylene chloride and treating with 1.2 molar equivalent of 1,1'-carbonyldiimidazole (CDI) and 1.1 equivalent of 1,8-diazabicyclo[5.4.0]undec-7-ene (DBU) at room temperature and allowed to stir for 4 hrs under an argon atmosphere. After the initial reaction is completed, freshly prepared compound (9) (1.2 molar equivalent) is added slowly to the reaction at room temperature while stirring. The resulting mixture is allowed to stir for an additional 4 hrs to produce the desired compound (10).

Schemes 4-10 demonstrate the actual synthesis that has been performed to arrive at some of the compounds of the invention. These schemes and description of reaction conditions are outlined below.

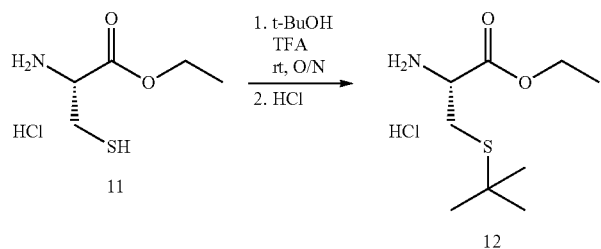
Scheme 4
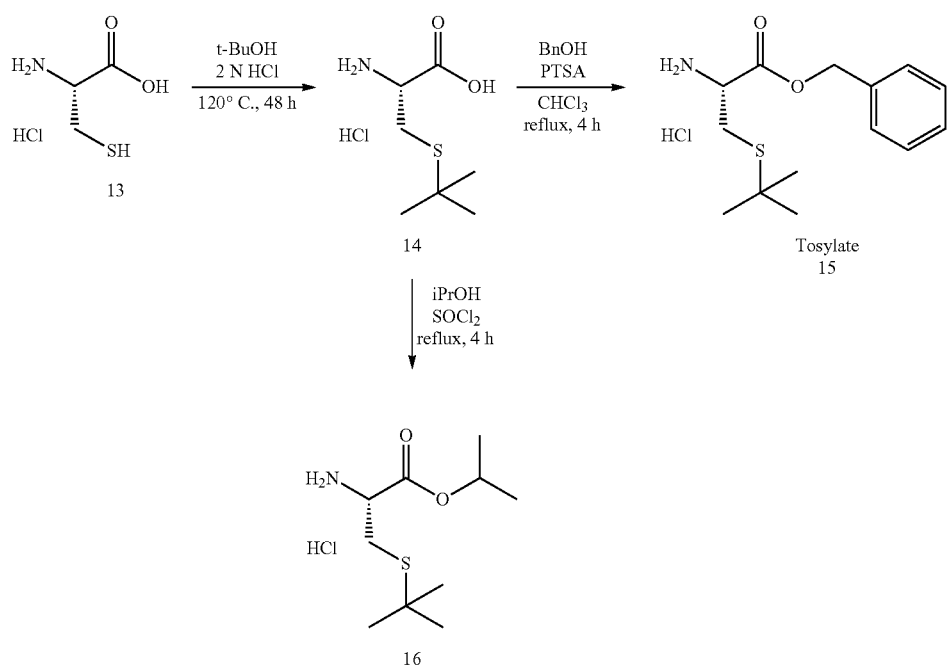
Scheme 5
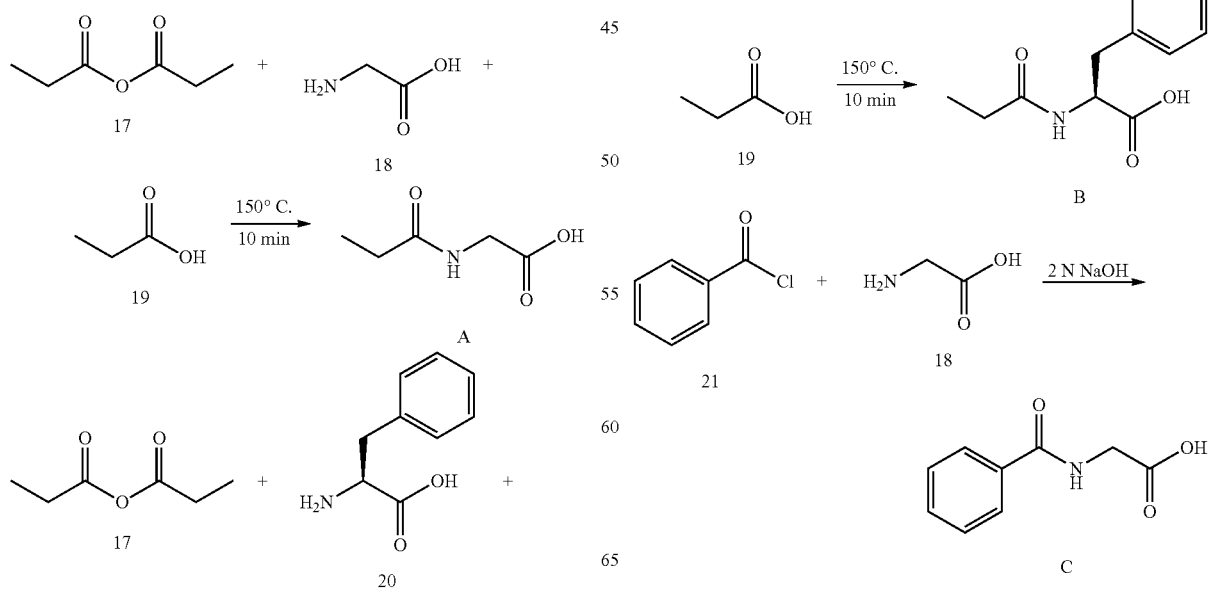

Scheme 6
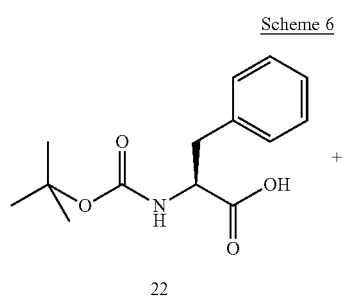
22
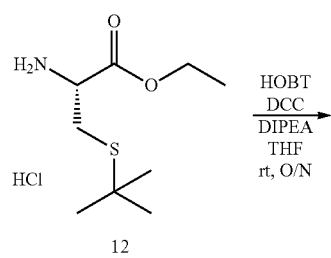
12
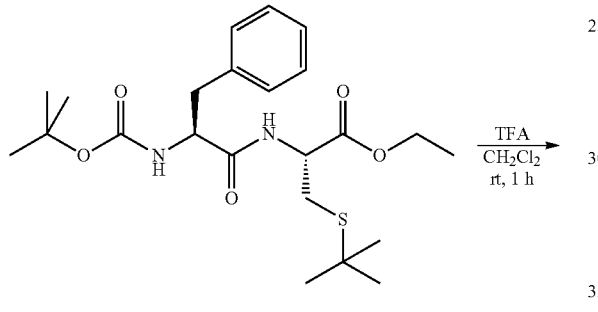
23
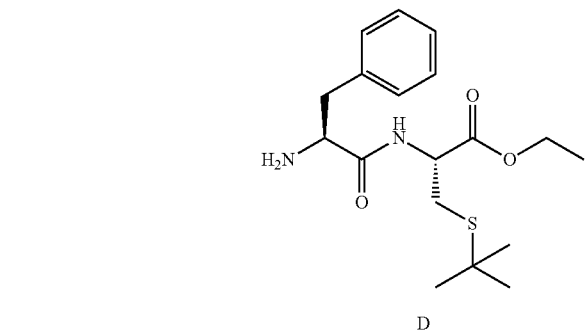
D
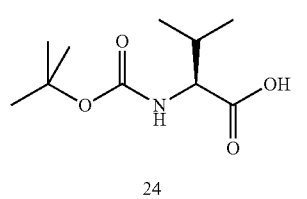
24
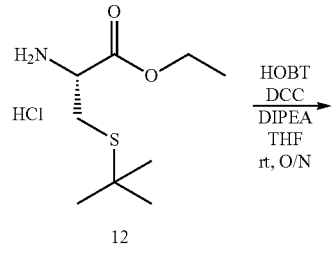
12
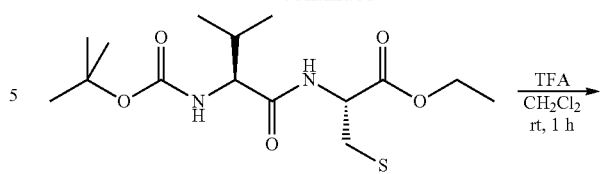
25
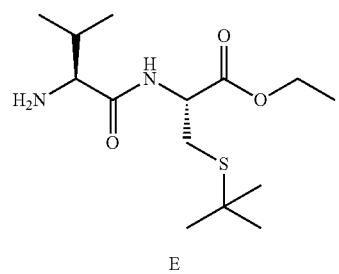
E
Scheme 7
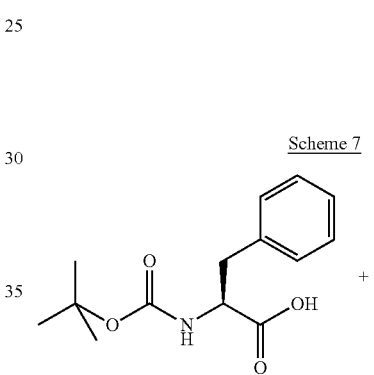
22
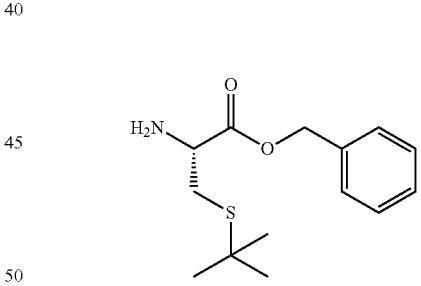
Tosylate 15
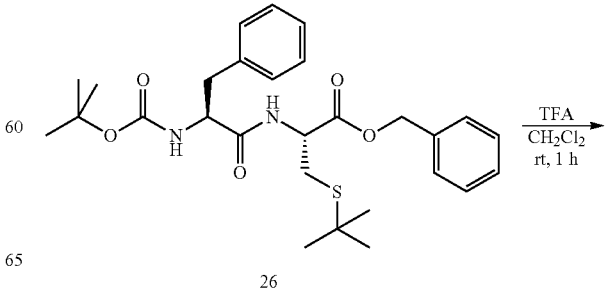
26

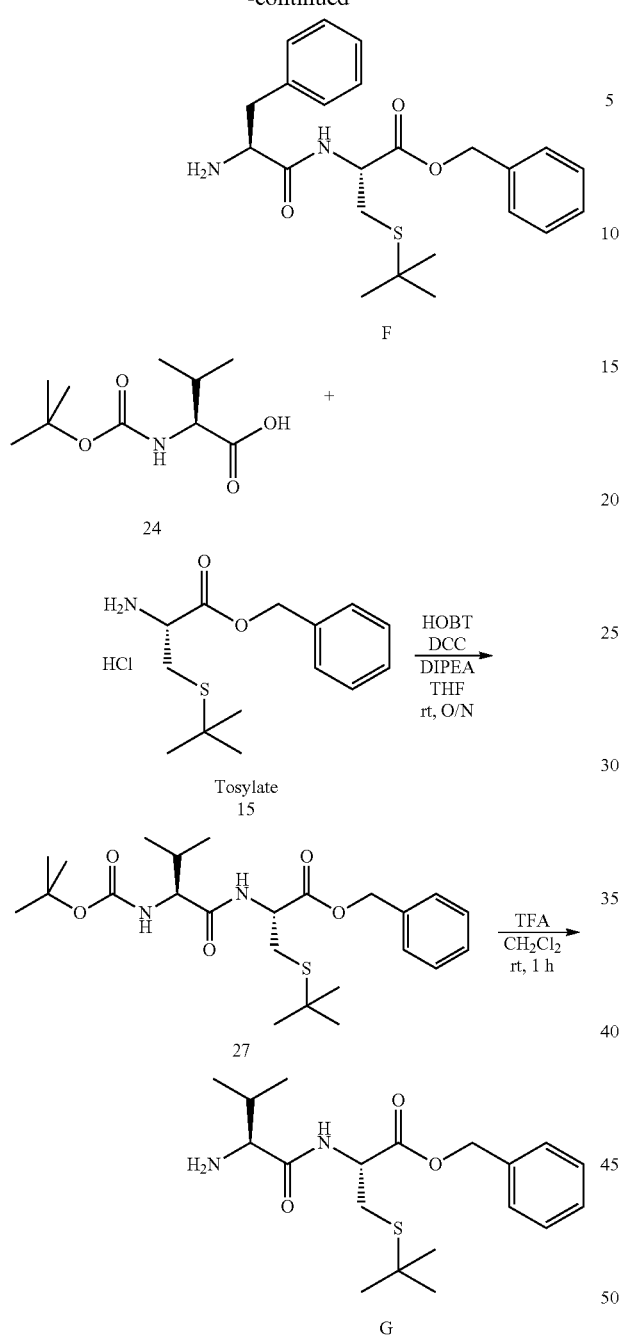
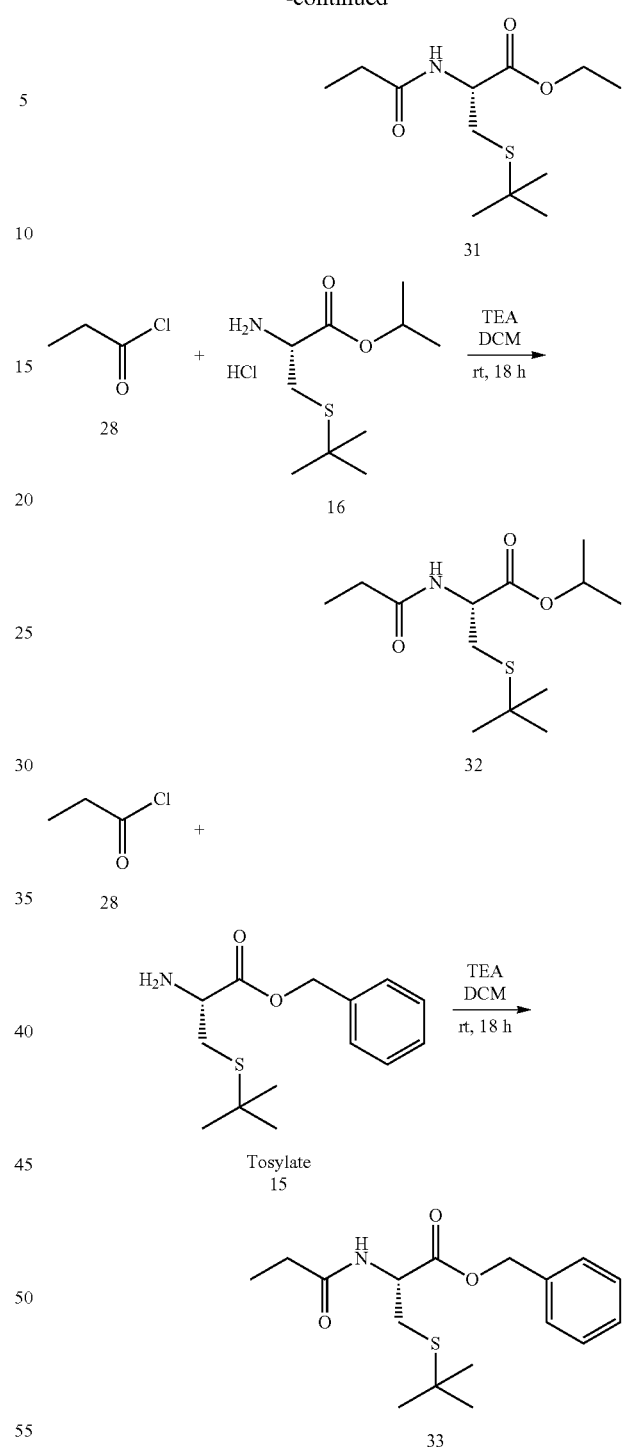
Scheme 8
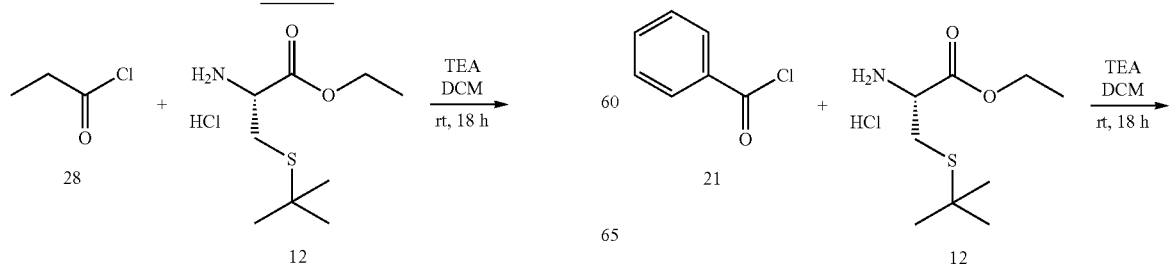

27
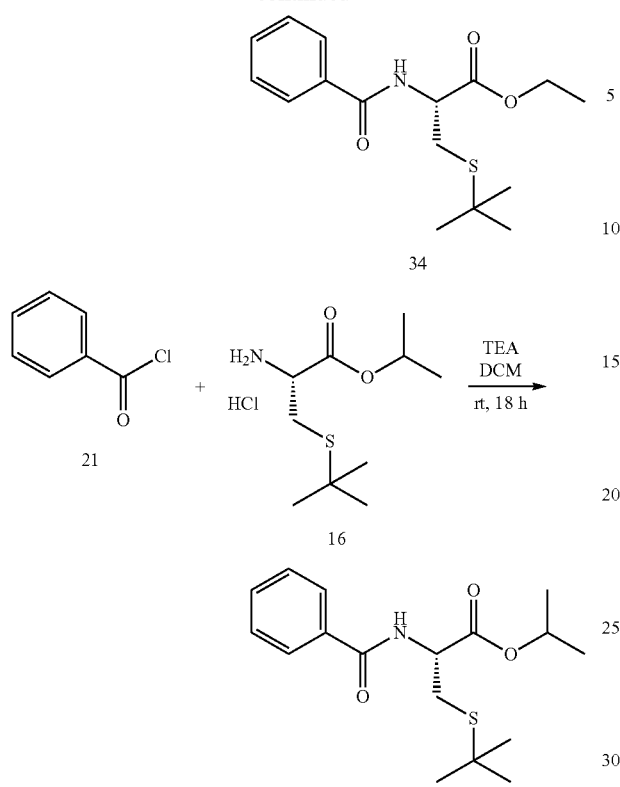
Scheme 9
28
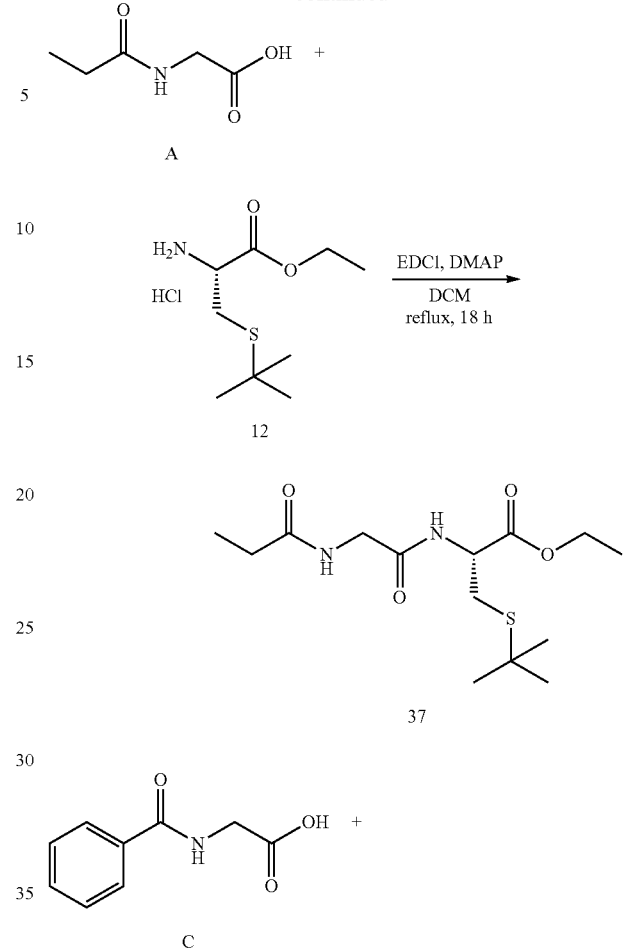
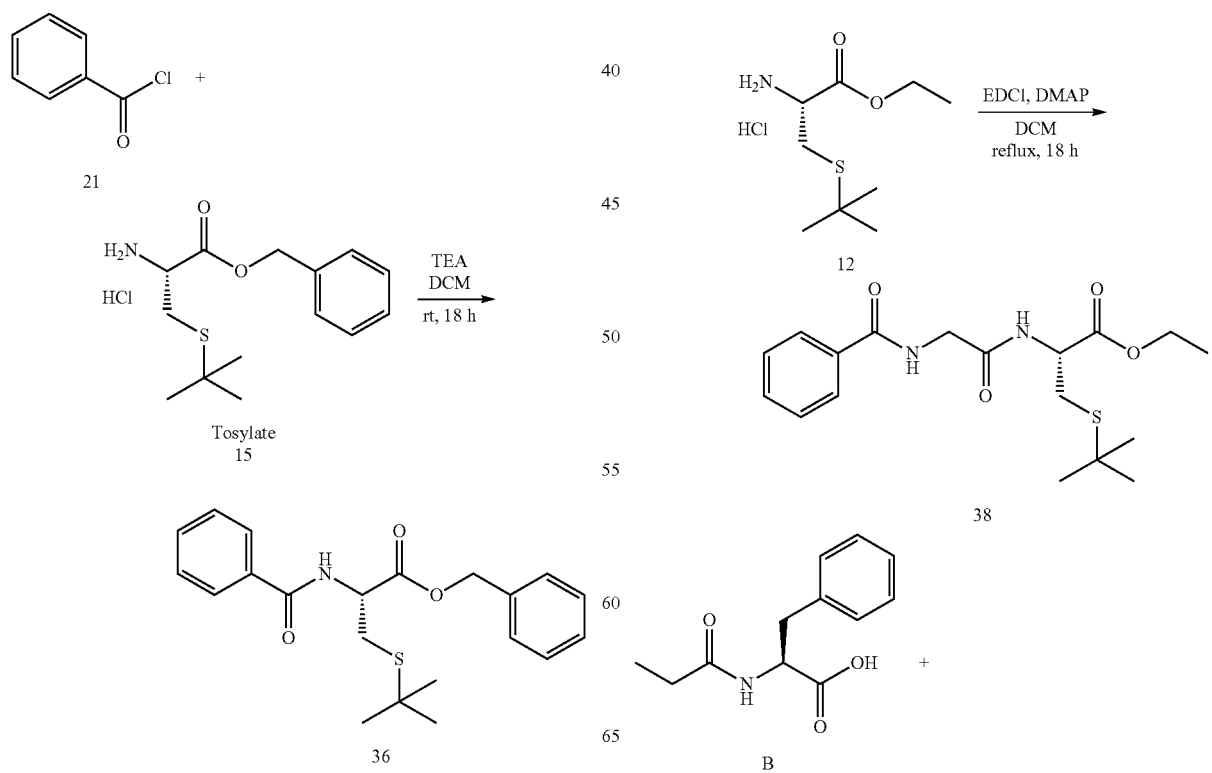

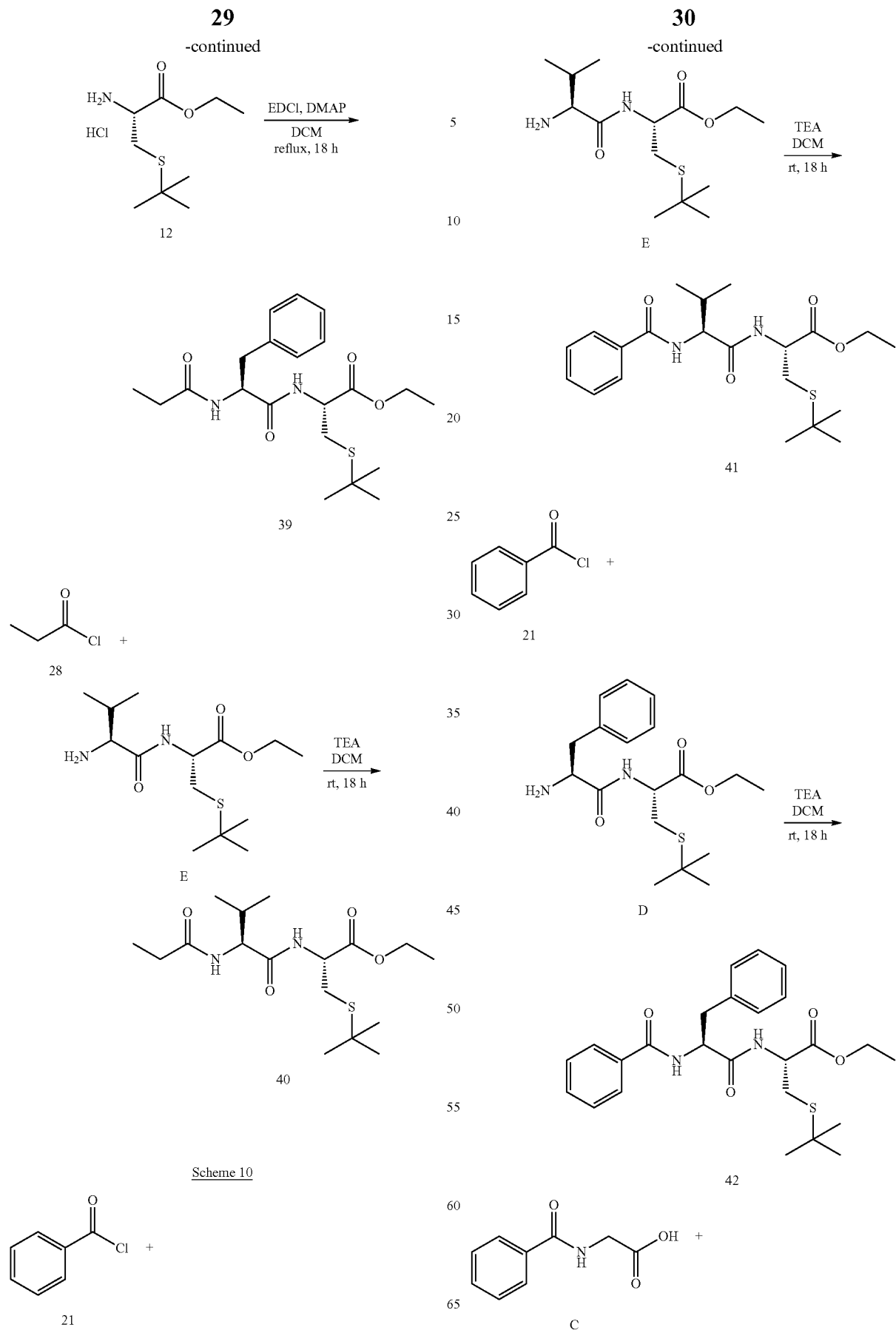

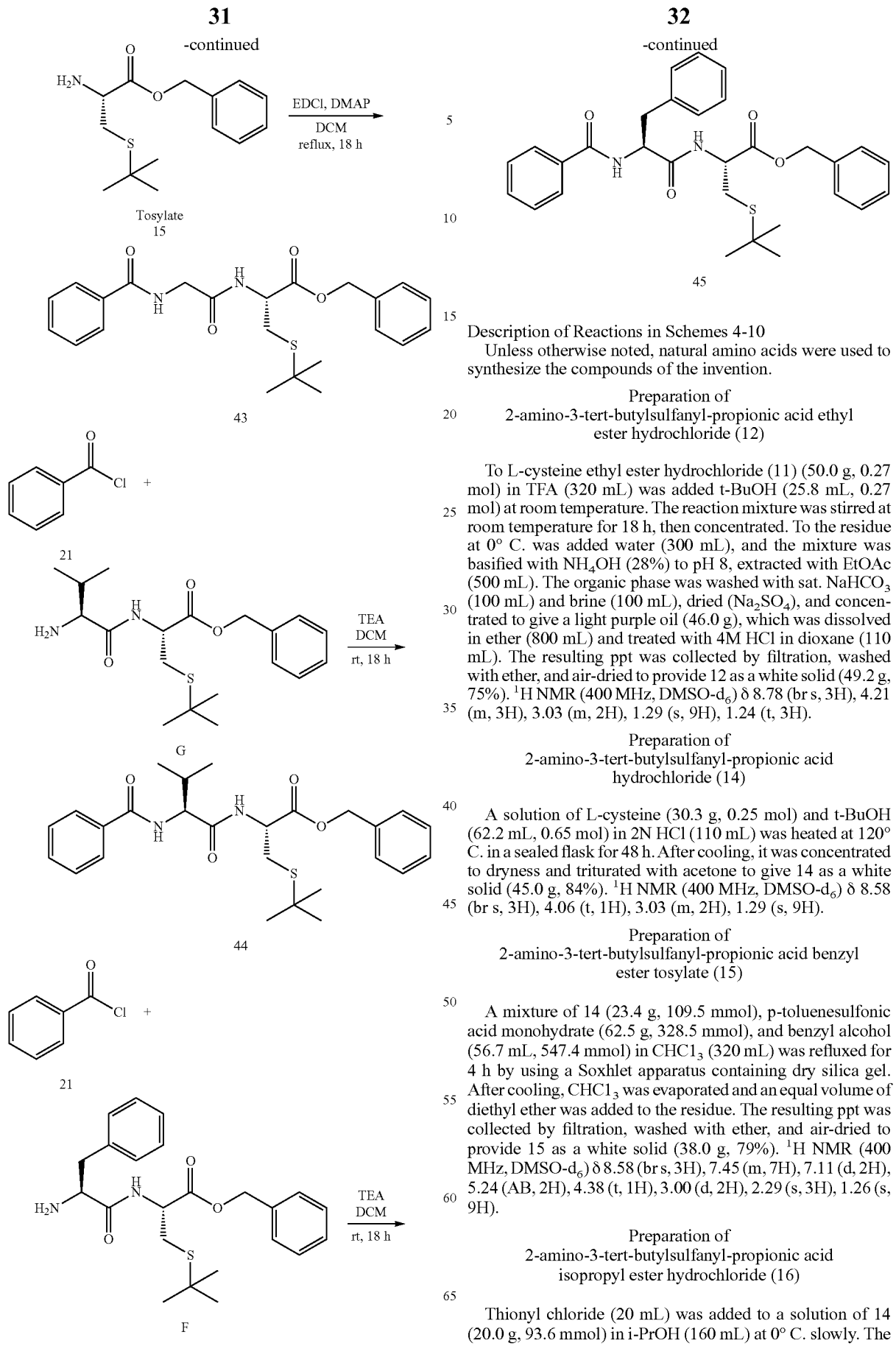

Description of Reactions in Schemes 4-10

Unless otherwise noted, natural amino acids were used to synthesize the compounds of the invention.

Preparation of 2-amino-3-tert-butylsulfanyl-propionic acid ethyl ester hydrochloride (12)

To L-cysteine ethyl ester hydrochloride (11) (50.0 g, 0.27 mol) in TFA (320 mL) was added t-BuOH (25.8 mL, 0.27 mol) at room temperature. The reaction mixture was stirred at room temperature for 18 h, then concentrated. To the residue at 0° C. was added water (300 mL), and the mixture was basified with $NH_4OH$ (28%) to pH 8, extracted with EtOAc (500 mL). The organic phase was washed with sat. $NaHCO_3$ (100 mL) and brine (100 mL), dried ($Na_2SO_4$), and concentrated to give a light purple oil (46.0 g), which was dissolved in ether (800 mL) and treated with 4M HCl in dioxane (110 mL). The resulting ppt was collected by filtration, washed with ether, and air-dried to provide 12 as a white solid (49.2 g, 75%). $^1$H NMR (400 MHz, DMSO-$d_6$) δ 8.78 (br s, 3H), 4.21 (m, 3H), 3.03 (m, 2H), 1.29 (s, 9H), 1.24 (t, 3H).

Preparation of 2-amino-3-tert-butylsulfanyl-propionic acid hydrochloride (14)

A solution of L-cysteine (30.3 g, 0.25 mol) and t-BuOH (62.2 mL, 0.65 mol) in 2N HCl (110 mL) was heated at 120° C. in a sealed flask for 48 h. After cooling, it was concentrated to dryness and triturated with acetone to give 14 as a white solid (45.0 g, 84%). $^1$H NMR (400 MHz, DMSO-$d_6$) δ 8.58 (br s, 3H), 4.06 (t, 1H), 3.03 (m, 2H), 1.29 (s, 9H).

Preparation of 2-amino-3-tert-butylsulfanyl-propionic acid benzyl ester tosylate (15)

A mixture of 14 (23.4 g, 109.5 mmol), p-toluenesulfonic acid monohydrate (62.5 g, 328.5 mmol), and benzyl alcohol (56.7 mL, 547.4 mmol) in $CHCl_3$ (320 mL) was refluxed for 4 h by using a Soxhlet apparatus containing dry silica gel. After cooling, $CHCl_3$ was evaporated and an equal volume of diethyl ether was added to the residue. The resulting ppt was collected by filtration, washed with ether, and air-dried to provide 15 as a white solid (38.0 g, 79%). $^1$H NMR (400 MHz, DMSO-$d_6$) δ 8.58 (br s, 3H), 7.45 (m, 7H), 7.11 (d, 2H), 5.24 (AB, 2H), 4.38 (t, 1H), 3.00 (d, 2H), 2.29 (s, 3H), 1.26 (s, 9H).

Preparation of 2-amino-3-tert-butylsulfanyl-propionic acid isopropyl ester hydrochloride (16)

Thionyl chloride (20 mL) was added to a solution of 14 (20.0 g, 93.6 mmol) in i-PrOH (160 mL) at 0° C. slowly. The reaction mixture was refluxed for 4 h, then cooled and concentrated. The residue was treated with ether (200 mL). The resulting ppt was collected by filtration, washed with ether, and air-dried to provide 16 as a white solid (19.7 g, 82%). $^1$H NMR (400 MHz, DMSO-$d_6$) δ 8.78 (br s, 3H), 5.00 (m, 1H), 4.14 (t, 1H), 3.03 (m, 2H), 1.29 (s, 9H), 1.26 (d, 3H), 1.24 (d, 3H).

General Procedure A: Preparation of propionylamino-acetic acid (A) (09-031-41)

A mixture of 17 (46 mL, 357 mmol) and 18 (10.0 g, 133 mmol) in 19 (164 mL) was heated at 150° C. for 10 min. After cooling, water (100 mL) was added, and the mixture was concentrated. EtOAc (50 mL) was added, the resulting ppt was collected by filtration, washed with EtOAc (10 mL), and air-dried to provide A as a white solid (12.0 g, 92%) after treated with charcoal. $^1$H NMR (400 MHz, DMSO-$d_6$) δ 12.50 (br s, 1H), 8.08 (br t, 1H), 3.72 (d, 2H), 2.22 (q, 2H), 0.99 (t, 3H).

Preparation of 3-phenyl-2-propionylamino-propionic acid (B)

With General procedure A, starting from 17 (46 mL, 357 mmol) and 20 (22.0 g, 133 mmol) in 19 (164 mL), 21.0 g (71%) of B was obtained as a white solid. $^1$H NMR (400 MHz, DMSO-$d_6$) δ 12.65 (br s, 1H), 8.08 (d, 1H), 7.26 (m, 5H), 4.40 (m, 1H), 3.04 (m, 1H), 2.84 (m, 1H), 2.06 (m, 2H), 0.90 (t, 3H).

Preparation of Benzoylamino-Acetic Acid (C)

Compound 18 (10 g, 133 mmol) was dissolved in 10% sodium hydroxide solution (100 mL), cooled to 15° C., and then benzoyl chloride 21 (21.6 mL, 186 mmol) was added in portions to this solution. After the addition, the mixture was stirred at room temperature for 0.5 h. Crushed ice (100 g) was added to the solution and concentrated HCl was added dropwise until the mixture was acidified (pH 2-3). The resulting compound C (23 g, 96%) was obtained as a white solid. $^1$H NMR (400 MHz, CD$_3$OD) δ 8.73 (br s, 1H), 7.87 (d, 2H), 7.54 (m, 3H), 4.87 (br s, 1H), 4.10 (s, 2H).

General Procedure B: Preparation of 2-(2-tert-butoxycarbonylamino-3-phenyl-propionylamino)-3-tert-butylsulfanyl-propionic acid ethyl ester (23)

To a mixture of 22 (6.63 g, 25.0 mmol), 12 (6.04 g, 25.0 mmol), HOBt (3.72 g, 27.5 mmol), and DIPEA (4.35 mL, 25.0 mmol) in THF (150 mL) was added DCC (5.67 g, 27.5 mmol) in THF (50 mL). The reaction mixture was stirred at room temperature for 18 h, then EtOAc (200 mL) was added. The mixture was washed successively with 1N HCl (50 mL), sat. NaHCO$_3$ (50 mL), and brine (50 mL), dried (Na$_2$SO$_4$), and concentrated. Silica gel chromatography (hexanes/EtOAc 4:1) gave 23 as a colorless sticky mass (8.87 g, 78%). $^1$H NMR (400 MHz, CDCl$_3$) δ 7.26 (m, 5H), 6.60 (br d, 1H), 4.99 (br d, 1H), 4.75 (m, 1H), 4.40 (br d, 1H), 4.20 (m, 2H), 3.10 (m, 2H), 2.95 (m, 2H), 1.40 (s, 9H), 1.26 (m, 12H).

General Procedure C: Preparation of 2-(2-amino-3-phenyl-propionylamino)-3-tert-butylsulfanyl-propionic acid ethyl ester (D)

To a solution of 23 (6.63 g, 25.0 mmol) in CH$_2$Cl$_2$ (30 mL) was added TFA (30 mL) dropwise at 0° C. The reaction mixture was stirred at room temperature for 1 h, then concentrated. EtOAc (150 mL) was added, washed successively with sat. NaHCO$_3$ (2×20 mL) and brine (20 mL), dried (Na$_2$SO$_4$), and concentrated to give D as a light yellow oil (6.83 g, 99%). $^1$H NMR (400 MHz, CDCl$_3$) δ 7.94 (br d, 1H), 7.30 (m, 5H), 4.80 (m, 1H), 4.21 (q, 2H), 3.70 (dd, 1H), 3.28 (dd, 1H), 2.99 (m, 2H), 2.74 (dd, 1H), 2.25 (br s, 2H), 1.30 (m, 12H).

Preparation of 2-(2-tert-butoxycarbonylamino-3-methyl-butyrylamino)-3-tert-butylsulfanyl-propionic acid ethyl ester (25)

With General procedure B, starting from 24 (5.43 g, 25.0 mmol) and 12 (6.04 g, 25.0 mmol), 7.86 g (78%) of 25 was obtained as a white solid. $^1$H NMR (400 MHz, CDCl$_3$) δ 6.59 (br d, 1H), 5.06 (br d, 1H), 4.82 (m, 1H), 4.23 (q, 2H), 4.00 (t, 1H), 3.01 (d, 2H), 2.18 (m, 1H), 1.45 (s, 9H), 1.30 (m, 12H), 0.98 (d, 3H), 0.93 (d, 3H).

Preparation of 2-(2-amino-3-methyl-butyrylamino)-3-tert-butylsulfanyi-propionic acid ethyl ester (E)

With General procedure C, starting from 25 (7.86 g, 19.43 mmol), 6.87 g (crude) of E was obtained as a colorless sticky mass. $^1$H NMR (400 MHz, CDCl$_3$) δ 7.76 (br d, 1H), 4.79 (m, 1H), 4.23 (q, 2H), 3.49 (d, 1H), 3.00 (d, 2H), 2.27 (m, 1H), 1.30 (m, 12H), 1.02 (d, 3H), 0.95 (d, 3H).

Preparation of 2-(2-tert-butoxycarbonylamino-3-phenyl-propionylamino)-3-tert-butylsulfanyl-propionic acid benzyl ester (26)

With General procedure B, starting from 22 (6.63 g, 25.0 mmol) and 15 (10.99 g, 25.0 mmol), 11.60 g (90%) of 26 was obtained as a white gum. $^1$H NMR (400 MHz, CDCl$_3$) δ 7.38-7.18 (m, 10H), 6.60 (br d, 1H), 5.16 (AB, 2H), 5.00 (br s, 1H), 4.80 (m, 1H), 4.40 (br d, 1H), 3.07 (m, 2H), 2.96 (d, 2H), 1.40 (s, 9H), 1.22 (s, 9H).

Preparation of 2-(2-amino-3-phenyl-propionylamino)-3-tert-butylsulfanyl-propionic acid benzyl ester (F)

With General procedure C, starting from 26 (5.60 g, 10.88 mmol), 4.50 g (quant.) of F was obtained as a colorless sticky mass. $^1$H NMR (400 MHz, CDCl$_3$) δ 7.26 (m, 10H), 5.15 (s, 2H), 4.75 (m, 1H), 4.00 (m, 1H), 3.09 (m, 1H), 2.92 (m, 3H), 1.22 (s, 9H).

Preparation of 2-(2-tert-butoxycarbonylamino-3-methyl-butyrylamino)-3-tert-butylsulfanyl-propionic acid benzyl ester (27)

With General procedure B, starting from 24 (5.43 g, 25.0 mmol) and 15 (10.99 g, 25.0 mmol), 10.0 g (86%) of 27 was obtained as a white sticky mass. $^1$H NMR (400 MHz, CDCl$_3$) δ 7.36 (m, 5H), 6.59 (br d, 1H), 5.19 (s, 2H), 5.05 (br d, 1H), 4.89 (m, 1H), 4.00 (m, 1H), 3.01 (d, 2H), 2.15 (m, 1H), 1.44 (s, 9H), 1.27 (s, 9H), 0.95 (d, 3H), 0.90 (d, 3H).

Preparation of 2-(2-amino-3-methyl-butyrylamino)-3-tert-butylsulfanyl-propionic acid benzyl ester (G)

With General procedure C, starting from 27 (10.0 g, 21.4 mmol), 8.50 g (crude) of G was obtained as a colorless oil. $^1$H NMR (400 MHz, CDCl$_3$) δ 7.77 (br d, 1H), 7.36 (m, 5H), 5.19

(s, 2H), 4.88 (m, 1H), 3.40 (d, 1H), 3.00 (d, 2H), 2.26 (m, 1H), 1.28 (s, 9H), 0.99 (d, 3H), 0.89 (d, 3H).

General Procedure D: Preparation of 3-tert-butylsulfanyl-2-propionylamino-propionic acid ethyl ester (31)

To a mixture of 12 (11.40 g, 47.15 mmol) and triethylamine (15 mL, 108.0 mmol) in dichloromethane (180 mL) was added 28 (4.9 mL, 56.20 mmol) in dichloromethane (20 mL) dropwise at 0° C. The mixture was stirred at room temperature for 18 h, and evaporated. The residue was dissolved in ethyl acetate (200 mL), washed with 10% HCl, water, saturated sodium bicarbonate, brine, dried and evaporated. The residue was purified by column chromatography using EtOAc:Hexane (1:4) as eluent to give the title compound (7.39 g, 60%) as a thick oil. $^1$H NMR (400 MHz, CDCl$_3$) δ 6.25 (br s, 1H), 4.87 (m, 1H), 4.24 (q, 2H), 3.03 (d, 2H), 2.28 (q, 2H), 1.32 (m, 12H), 1.19 (t, 3H). MS m/z 262 (M+1). HPLC: 96.55% (ACQ_PA95_C_BLS; Column: BEH_C18_2–1×50 mm_1-7 μm).

Preparation of 3-tert-butylsulfanyl-2-propionylamino-propionic acid isopropyl ester (32)

With General procedure D, starting from 28 (4.63 g, 50.0 mmol) and 16 (10.23 g, 40 mmol), 7.16 g (65%) of the title compound was obtained as a colorless oil. $^1$H NMR (400 MHz, CDCl$_3$) δ 6.25 (br s, 1H), 5.06 (q, 1H), 4.85 (m, 1H), 3.03 (d, 2H), 2.30 (q, 2H), 1.29 (m, 15H), 1.17 (t, 3H). MS m/z 276 (M+1). HPLC: 95.29% (ACQ_PA95_C_BLS; Column: BEH_C18_2–1×50 mm_1-7 μm).

Preparation of 3-tert-butylsulfanyl-2-propionylamino-propionic acid benzyl ester (33)

With General procedure D, starting from 28 (4.43 g, 47.88 mmol) and 15 (14.61 g, 33.24 mmol), 5.37 g (50%) of the title compound was obtained as a colorless oil. $^1$H NMR (400 MHz, CDCl$_3$) δ 7.38 (m, 5H), 6.27 (br d, 1H), 5.20 (m, 2H), 4.94 (m, 1H), 3.03 (d, 2H), 2.29 (q, 2H), 1.27 (s, 9H), 1.17 (t, 3H). MS m/z 324 (M+1). HPLC: 98.52% (ACQ_PA95_C_BLS; Column: BEH_C18_2–1×50 mm_1-7 μm).

Preparation of 2-benzoylamino-3-tert-butylsulfanyl-propionic acid ethyl ester (34)

With General procedure D, starting from 21 (5.94 g, 42.26 mmol) and 12 (8.54 g, 35.36 mmol), 6.56 g (60%) of the title compound was obtained as a white solid. $^1$H NMR (400 MHz, CDCl$_3$) δ 7.83 (d, 2H), 7.52 (m, 3H), 6.97 (br d, 1H), 5.06 (m, 1H), 4.28 (q, 2H), 3.16 (m, 2H), 1.32 (m, 12H). MS m/z 310 (M+1). HPLC: 98.35% (ACQ_PA95_C_BLS; Column: BEH_C18_2–1×50 mm_1-7 μm).

Preparation of 2-Benzoylamino-3-tert-butylsulfanyl-propionic acid isopropyl ester (35)

With General procedure D, starting from 21 (5.6 g, 40.4 mmol) and 16 (7.33 g, 28.65 mmol), 6.72 g (73%) of the title compound was obtained as a white solid. $^1$H NMR (400 MHz, CDCl$_3$) δ 7.82 (m, 2H), 7.54-7.43 (m, 3H), 6.97 (br d, 1H), 5.12 (m, 1H), 5.02 (m, 1H), 3.14 (dd, 2H), 1.30 (m, 15H). MS m/z 324 (M+1). HPLC: 96.61% (ACQ_PA95_C_BLS; Column: BEH_C18_2–1×50 mm_1-7 μm).

Preparation of 2-Benzoylamino-3-tert-butylsulfanyl-propionic acid benzyl ester (36)

With General procedure D, starting from 21 (4.2 g, 30.2 mmol) and 15 (9.43 g, 21.45 mmol), 5.18 g (65%) of the title compound was obtained as a yellow solid. $^1$H NMR (400 MHz, CDCl$_3$) δ 7.82 (d, 2H), 7.50 (m, 8H), 6.98 (br d, 1H), 5.27 (m, 2H), 5.12 (m, 1H), 3.15 (m, 2H), 1.27 (s, 9H). MS m/z 372 (M+1). HPLC: 96.80% (ACQ_PA95_C_BLS; Column: BEH_C18_2–1×50 mm_1-7 μm).

General procedure E: Preparation of 3-tert-Butylsulfanyl-2-(2-propionylamino-acetylamine)-propionic acid ethyl ester (37)

To a mixture of A (6.55 g, 50 mmol), 12 (12.09 g, 50 mmol), and 1-ethyl-(3-dimethylaminopropyl)carbodiimide hydrochloride (15.34 g, 80 mmol) in dichloromethane (700 mL) was added 4-(dimethylamino)pyridine (9.15 g, 75 mmol) at room temperature. The mixture was stirred at 40° C. overnight. After cooling down, to the mixture was added dichloromethane (500 mL), washed with 10% HCl (300 mL), saturated sodium bicarbonate (2×300 mL), brine (300 mL), dried over sodium sulfate and evaporated. The residue was purified by column chromatography using CH$_2$Cl$_2$/EtOAc/MeOH (70:28:2) as eluent to afford the title compound (6.20 g, 39%) as a light yellow oil. $^1$H NMR (400 MHz, CDCl$_3$) δ 6.66 (br d, 1H), 6.18 (br s, 1H), 4.81 (m, 1H), 4.23 (m, 2H), 4.00 (dd, 2H), 3.01 (d, 2H), 2.28 (q, 2H), 1.30 (m, 12H), 1.87 (t, 3H). MS m/z 319 (M+1). HPLC: 95.65% (ACQ_PA95_C_BLS; Column: BEH_C18_2–1×50 mm_1-7 μm).

Preparation of 2-(2-Benzoylamino-acetylamino)-3-tert-butylsulfanyl-propionic acid ethyl ester (38)

With General procedure E, starting from C (4.20 g, 23.4 mmol) and 12 (5.66 g, 23.4 mmol), 6.0 g (70%) of the title compound was obtained as a white solid. $^1$H NMR (400 MHz, CDCl$_3$) δ 7.85 (d, 2H), 7.53 (m, 3H), 7.18 (br s, 1H), 7.07 (br d, 1H), 4.87 (m, 1H), 4.25 (m, 4H), 3.03 (d, 2H), 1.30 (m, 12H). MS m/z 367 (M+1). HPLC: 98.57% (ACQ_PA95_C_BLS; Column: BEH_C18_2–1×50 mm_1-7 μm).

Preparation of 3-tert-Butylsulfanyl-2-(3-phenyl-2-propionylamino-propionylamino)-propionic acid ethyl ester (39)

With General procedure E, starting from B (13.26 g, 60.0 mmol) and 12 (12.32 g, 51.0 mmol), 4.1 g (16.7%) of the title compound was obtained as a white solid. $^1$H NMR (400 MHz, CDCl$_3$) δ 7.31 (m, 5H), 6.46 (br d, 1H), 6.07 (br d, 1H), 4.73 (q, 2H), 4.23 (m, 2H), 3.10 (d, 2H), 2.94 (d, 2H), 2.23 (q, 2H), 1.31 (m, 12H), 1.13 (t, 3H). MS m/z 409 (M+1). HPLC: 95.56% (ACQ_PA95_C_BLS; Column: BEH_C18_2–1×50 mm_1-7 μm).

Preparation of 3-tert-Butylsulfanyl-2-(3-methyl-2-propionylamino-butyrylamino)-propionic acid ethyl ester (40)

With General procedure D, starting from 28 (4.03 g, 43.55 mmol) and E (10.55 g, 34.65 mmol), 7.05 g (57%) of the title compound was obtained as a white solid. ¹H NMR (400 MHz, CDCl₃) δ 6.54 (br d, 1H), 6.09 (br d, 1H), 4.80 (m, 1H), 4.38 (dd, 1H), 4.22 (q, 2H), 3.00 (m, 2H), 2.26 (q, 2H), 2.11 (m, 1H), 1.29 (m, 12H), 1.17 (t, 3H), 0.97 (2d, 6H). MS m/z 361 (M+1). HPLC: 97.42% (ACQ_PA95_B_BLS; Column: BEH_C18_2–1×50 mm_1-7 μm).

Preparation of 2-(2-Benzoylamino-3-methyl-butyry-lamino)-3-tert-butylsulfanyl-propionic acid ethyl ester (41)

With General procedure D, starting from 21 (4.8 g, 34.15 mmol) and E (9.23 g, 30.32 mmol), 5.60 g (45%) of the title compound was obtained as a white solid. ¹H NMR (400 MHz, CDCl₃) δ 7.81 (m, 2H), 7.54-7.42 (m, 3H), 6.82 (br d, 1H), 6.59 (br d, 1H), 4.83 (m, 1H), 4.59 (dd, 1H), 4.23 (q, 2H), 3.01 (m, 2H), 2.24 (m, 1H), 1.30 (t, 3H), 1.27 (s, 9H), 1.06 (d, 3H), 1.04 (d, 3H). MS m/z 409 (M+1). HPLC: 98.20% (ACQ_PA95_C_BLS; Column: BEH_C18_2–1×50 mm_1-7 μm).

Preparation of 2-(2-Benzoylamino-3-phenyl-propionylamino)-3-tert-butylsulfanyl-propionic acid ethyl ester (42)

With General procedure D, starting from 21 (6.78 g, 48.23 mmol) and D (15.0 g, 42.55 mmol), 10.12 g (52%) of the title compound was obtained as a white solid. ¹H NMR (400 MHz, CDCl₃) δ 7.73 (m, 2H), 7.54-7.30 (m, 3H), 7.27 (m, 5H), 6.85 (br d, 1H), 6.56 (br d, 1H), 4.93 (q, 1H), 4.73 (m, 1H), 4.21 (m, 2H), 3.22 (m, 2H), 2.94 (d, 2H), 1.29 (t, 3H), 1.23 (s, 9H). MS m/z 457 (M+1). HPLC: 98.50% (ACQ_PA95_C_BLS; Column: BEH_C18_2–1×50 mm_1-7 μm).

Preparation of 2-(2-Benzoylamino-acetylamino)-3-tert-butylsulfanyl-propionic acid benzyl ester (43)

With General procedure E, starting from C (4.48 g, 25.0 mmol) and 15 (11.0 g, 25.0 mmol), 3.85 g (36%) of the title compound was obtained as white crystals. ¹H NMR (400 MHz, CDCl₃) δ 7.82 (m, 2H), 7.54-7.41 (m, 3H), 7.35 (m, 5H), 7.01 (br t, 1H), 6.93 (br d, 1H), 5.19 (s, 2H), 4.90 (m, 1H), 4.21 (m, 2H), 3.02 (d, 2H), 1.26 (s, 9H). MS m/z 429 (M+1). HPLC: 95.26% (ACQ_PA95_C_BLS; Column: BEH_C18_2–1×50 mm_1-7 μm).

Preparation of 2-(2-Benzoylamino-3-methyl-butyry-lamino)-3-tert-butylsulfanyl-propionic acid benzyl ester (44)

With General procedure D, starting from 21 (5.64 g, 40.12 mmol) and G (13.0 g, 35.47 mmol), 5.2 g (31%) of the title compound was obtained as a white solid. ¹H NMR (400 MHz, CDCl₃) δ 7.81 (d, 2H), 7.52 (m, 8H), 6.83 (br d, 1H), 6.68 (br d, 1H), 5.19 (s, 2H), 4.91 (m, 1H), 4.61 (t, 1H), 3.06 (m, 2H), 2.23 (m, 1H), 1.24 (s, 9H), 1.02 (d, 6H). MS m/z 471 (M+1). HPLC: 96.20% (ACQ_PA95_C_BLS; Column: BEH_C18_2–1×50 mm_1-7 μm).

Preparation of 2-(2-Benzoylamino-3-phenyl-propionylamino)-3-tert-butylsulfanyl-propionic acid benzyl ester (45)

With General procedure D, starting from 21 (3.68 g, 26.18 mmol) and F (9.2 g, 22.19 mmol), 5.1 g (44%) of the title compound was obtained as a white solid. ¹H NMR (400 MHz, CDCl₃) δ 7.73 (d, 2H), 7.52 (m, 13H), 6.81 (br d, 1H), 6.48 (br d, 1H), 5.23 (q, 2H), 4.92 (q, 1H), 4.79 (m, 1H), 3.26 (m, 2H), 2.95 (d, 2H), 1.20 (s, 9H). MS m/z 519 (M+1). HPLC: 96.38% (ACQ_PA95_C_BLS; Column: BEH_C18_2–1×50 mm_1-7 μm).

What is claimed is:

1. A compound selected from the group consisting of:

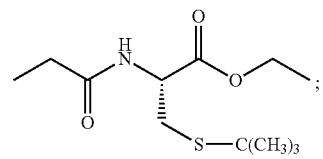

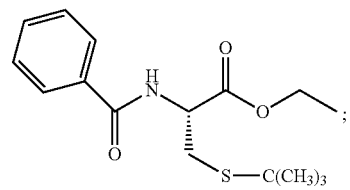

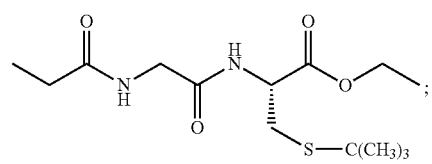

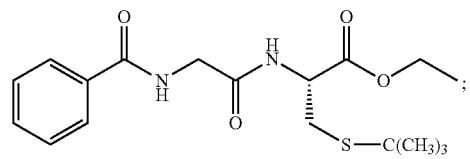

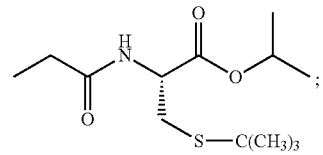

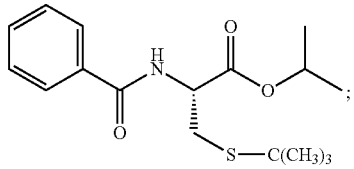

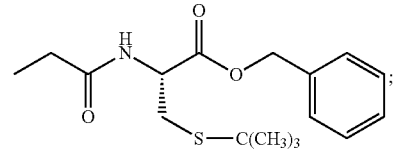

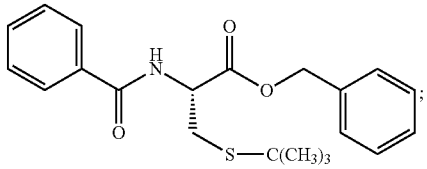

-continued
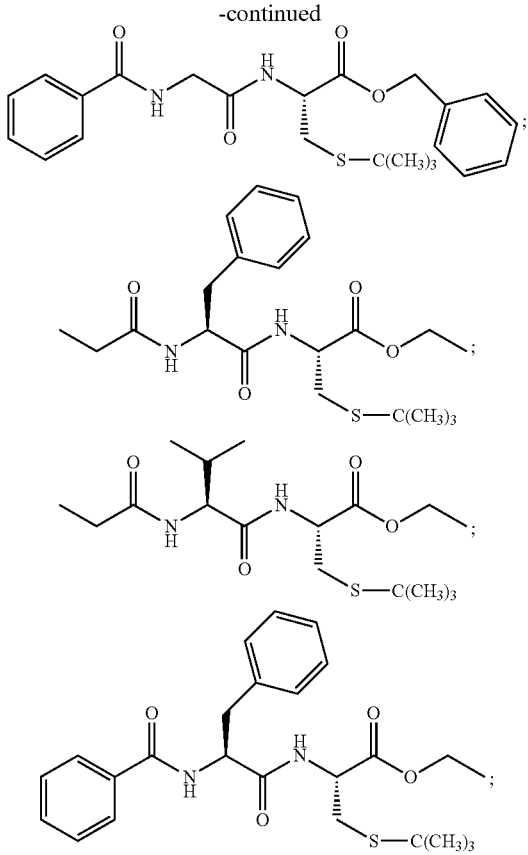
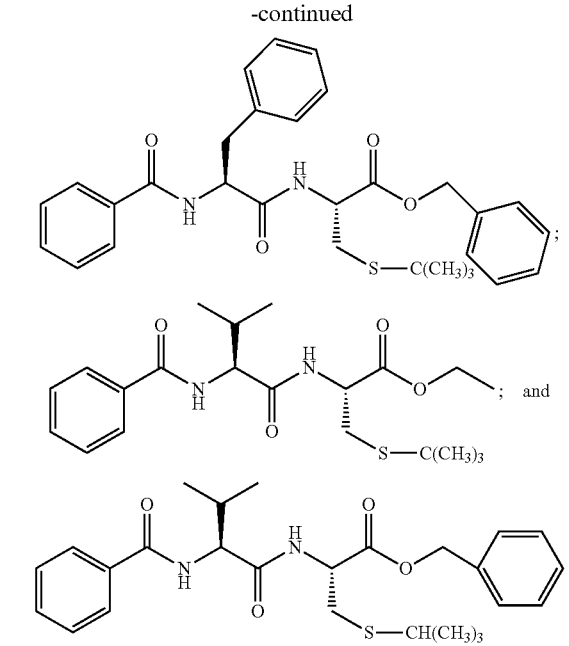
or a pharmaceutically acceptable salt, ester or prodrug thereof.
2. A pharmaceutical composition comprising at least one compound of claim 1 and a pharmaceutically acceptable carrier.
* * * * *